United States Patent
Wan et al.

(10) Patent No.: US 11,427,526 B2
(45) Date of Patent: Aug. 30, 2022

(54) METHOD OF PREPARING HYDROXYTYROSOL CINNAMIC ACID ESTER WITH ANTIOXIDANT AND ANTIBACTERIAL ACTIVITIES

(71) Applicants: Jia Wan, Xi'an (CN); Jie Zhang, Xi'an (CN); Chunchun Kong, Xi'an (CN); Yi Jin, Xi'an (CN); Min Fan, Xi'an (CN); Han Li, Xi'an (CN); Qiaoqiao Zhao, Xi'an (CN); Dan Yang, Xi'an (CN)

(72) Inventors: Jia Wan, Xi'an (CN); Jie Zhang, Xi'an (CN); Chunchun Kong, Xi'an (CN); Yi Jin, Xi'an (CN); Min Fan, Xi'an (CN); Han Li, Xi'an (CN); Qiaoqiao Zhao, Xi'an (CN); Dan Yang, Xi'an (CN)

(73) Assignee: XI'AN KANGYUANSHENG BIOMEDICAL TECHNOLOGY CO., LTD., Xi'an (CN)

( * ) Notice: Subject to any disclaimer, the term of this patent is extended or adjusted under 35 U.S.C. 154(b) by 154 days.

(21) Appl. No.: 17/026,224

(22) Filed: Sep. 19, 2020

(65) Prior Publication Data
US 2022/0089518 A1 Mar. 24, 2022

(51) Int. Cl.
C07C 67/40 (2006.01)
A01N 37/00 (2006.01)
C07C 69/73 (2006.01)

(52) U.S. Cl.
CPC .............. *C07C 67/40* (2013.01); *A01N 37/00* (2013.01); *C07C 69/73* (2013.01)

(58) Field of Classification Search
CPC ......... C07C 67/40; C07C 69/73; C07C 67/08; A01N 37/00
See application file for complete search history.

*Primary Examiner* — Deborah D Carr
(74) *Attorney, Agent, or Firm* — SZDC Law P.C.

(57) ABSTRACT

A method of preparing a compound of formula (I):

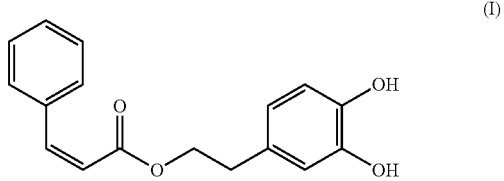

is disclosed. The compound of formula (I) can be used as an antioxidant agent. The compound can also be used as an antibacterial agent to inhibit *Staphylococcus aureus* MRSA 18-222 and *Pseudomonas aeruginosa* MDR-PA 18-1774.

13 Claims, 1 Drawing Sheet

METHOD OF PREPARING HYDROXYTYROSOL CINNAMIC ACID ESTER WITH ANTIOXIDANT AND ANTIBACTERIAL ACTIVITIES

FIELD OF THE INVENTION

The present invention relates to the field of medicinal chemistry, and in particular, to a hydroxytyrosol cinnamic acid ester with antioxidant and antibacterial activities.

BACKGROUND OF THE INVENTION

In recent years, various antibiotics and antimicrobial-resistant bacteria have developed rapidly. The emergence of methicillin-resistant *Straphylococcus aureus* (MRSA), penicillin-resistant *Streptococcus pneumoniae* (PRSP), multi-resistant tuberculosis, especially vancomycin-resistant *Enterococcus* (VRE), has caused difficulties in clinical treatment. Since the existing drugs are still difficult to effectively control the infection of these resistant bacteria, the research on anti-drug resistant bacteria has attracted much attention.

Olive fruits are rich in various phenolic compounds. A large number of pharmacological studies have shown that the effective effects of olives and olive extracts are likely caused by the phenolic substances in olives. Current research has found antioxidant phenols in fruits, vegetables, wine, tea, cocoa drinks, and fresh olive oil. Hydroxytyrosol (compound of formula II) is the most effective one among them, which shows a lot of beneficial properties, such as cancer chemoprevention, anti-atherosclerosis, inhibition of DNA oxidative damage, protection of skin against photodamage, and anti-inflammatory activities.

Cinnamic acid (compound of formula III) extracted from natural plants is an aromatic fatty acid and is the deamination product of phenylalanine in plant tissues. It is an important intermediate for fine chemical synthesis, widely used in chemical products such as medicine, spices, plastics and photosensitive resin.

In the present invention, hydroxytyrosol is modified by cinnamic acid structure to obtain a hydroxytyrosol cinnamic acid ester that has excellent antibacterial activity and has high medical research and application value in the treatment of infectious diseases caused by multidrug resistant bacteria.

SUMMARY OF THE INVENTION

In one embodiment, a method includes reacting a compound of formula (II) with a compound of formula (III) to obtain a compound of formula (I), preparing a composition that includes the compound of formula (I); and applying the composition as an antioxidant agent.

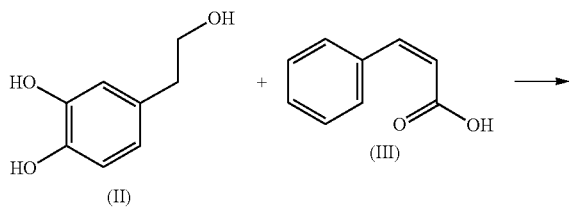

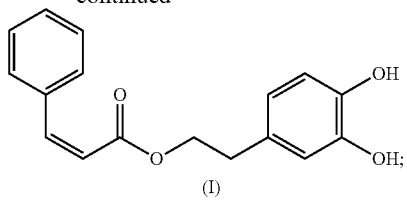

In another embodiment, the method further includes applying the composition as an antibacterial agent to inhibit *Straphylococcus aureus* MRSA 18-222 and *Pseudomonas aeruginosa* MDR-PA 18-1774.

In another embodiment, the reaction of the compound of formula (II) with the compound of formula (III) includes the following steps: placing the compound of formula (II) and the compound of formula (III), in a molar ratio of 1:1 to 1:1.3, in a reactor; adding an organic solvent and a catalytic amount of EDC to obtain a reaction mixture; and heating the reaction mixture at 50-80° C. for 4-8 hours; and purifying the crude product on a silica gel fresh chromatography column with petroleum ether and ethyl acetate as an eluent to obtain the compound of formula (I).

In another embodiment, the organic solvent is toluene, tetrahydrofuran or acetonitrile.

In another embodiment, the organic solvent is acetonitrile.

In another embodiment, the molar ratio of the compound of formula (II) and the compound of formula (III) is 1:1.1.

In another embodiment, the reaction mixture is heated at 70° C.

In another embodiment, the reaction mixture is heated for 6 hours.

In another embodiment, the eluent is petroleum ether: ethyl acetate=3:10.

In another embodiment, the reaction of the compound of formula (II) with the compound of formula (III) comprises the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (III) to the reactor to form a reaction mixture; heating the reaction mixture at 25-50° C. for 5-10 hours; placing the reaction mixture in a separating funnel to separate a crude product; purifying the crude product by recrystallization in methanol to obtain the compound of formula (I); and recycling the ionic liquid.

In another embodiment, the ionic liquid is 1-octyl-3-methylimidazolium hexafluorophosphate, 1-hexyl-3-methylimidazolium tetrafluoroborate, or 1-butyl-3-methylimidazolium tetrafluoroborate ([BMIM][BF$_4$]).

In another embodiment, the ionic liquid is 1-butyl-3-methylimidazolium tetrafluoroborate ([BMIM][BF$_4$]).

In another embodiment, the molar ratio of the compound of formula (II) and the compound of formula (III) is 1:1.1.

In another embodiment, the reaction mixture is heated at 25° C.

In another embodiment, the reaction mixture is heated for 8 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incor- In the drawings.

DETAILED DESCRIPTION OF THE ILLUSTRATED EMBODIMENTS

Figure 1:
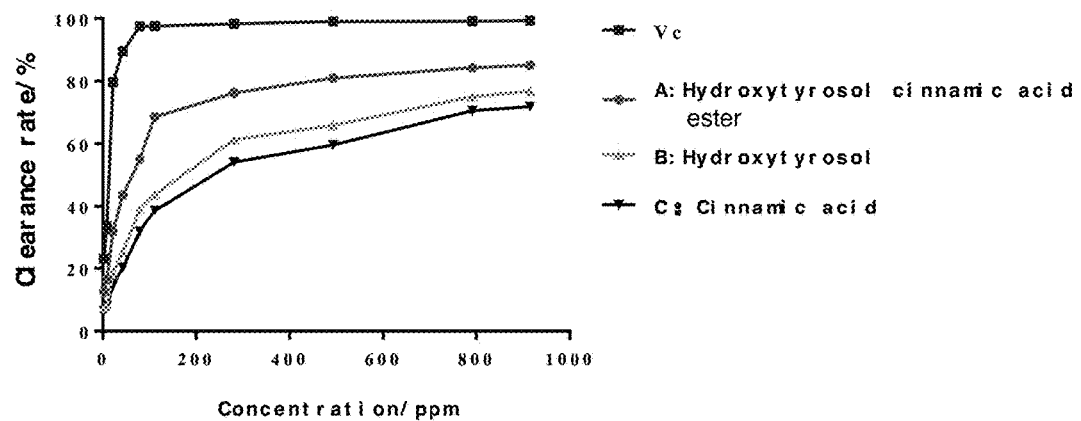
FIG. 1 shows the scavenging rate of the sample and control solution on DPPH free radicals.

Reference will now be made in detail to embodiments of the present invention, example of which is illustrated in the accompanying drawings. The following examples illustrate the present invention, but the present invention is not limited to the following examples.

EXAMPLE 1

Preparation of Compound
(Z)-3,4-Dihydroxyphenethyl 3-Phenylacrylate
(Compound of Cormula (I))

In a 100 mL three-necked flask, 49.3 mg (0.32 mmol) of hydroxytyrosol and 61.3 mg (0.32 mmol) EDC (1-ethyl-3-(3-dimethylaminopropyl)carbodiimide) were dissolved in 30 mL of acetonitrile under nitrogen atmosphere. 51.8 mg (0.35 mmol) of cinnamic acid was dissolved in 20 mL of acetonitrile, and slowly added dropwise to the reaction mixture by a separatory funnel. After the completion of the dropwise addition, the temperature was raised to 70° C., and the reaction was carried out for 6 hours. Thin layer chromatography was used to track the reaction to completion, heating was stopped, and the protective device was removed. The concentrated reaction mixture was washed wash water, extracted with ethyl acetate, dried and concentrated to obtain a crude product. The crude product was purified by silica gel column chromatography with petroleum ether:ethyl acetate=3:10 as eluent, and the eluent was concentrated under reduced pressure and dried to obtain 56.8 mg of the title compound, a total yield of 62.51%.

$^1$H-NMR (400 MHz, DMSO-$d_6$) δ (ppm): 7.71 (2H, d), 7.69 (2H, d), 7.64 (1H, d), 7.60 (1H, d), 7.44 (2H,d) 6.62 (1H, d), 6.46 (1H, d), 6.45 (2H, s), 3.56 (2H, t), 3.33 (2H, t); $^{13}$C-NMR (400 MHz, DMSO-$d_6$) δ ppm): 167.9, 145.3, 144.3, 143.7, 130.6, 129.3, 128.6, 119.8, 119.7, 116.7, 115.8, 63.0, 38.9.

EXAMPLE 2

Preparation of Compound
(Z)-3,4-Dihydroxyphenethyl 3-Phenylacrylate

In a 100 mL three-necked flask, 49.3 mg (0.32 mmol) of hydroxytyrosol and 61.3 mg (0.32 mmol) EDC were dissolved in 30 mL of toluene under nitrogen atmosphere. 51.8 mg (0.35 mmol) of cinnamic acid was dissolved in 20 mL of toluene, and slowly added dropwise to the reaction mixture by a separatory funnel. After the completion of the dropwise addition, the temperature was raised to 50° C., and the reaction was carried out for 6 hours. Thin layer chromatography was used to track the reaction to completion, heating was stopped, and the protective device was removed. The concentrated reaction mixture was washed wash water, extracted with ethyl acetate, dried and concentrated to obtain a crude product. The crude product was purified by silica gel column chromatography with petroleum ether:ethyl acetate=3:10 as eluent, and the eluent was concentrated under reduced pressure and dried to obtain 52.3 mg of the title compound, a total yield of 57.52%.

EXAMPLE 3

Preparation of Compound
(Z)-3,4-Dihydroxyphenethyl 3-Phenylacrylate

In a 100 mL three-necked flask, 49.3 mg (0.32 mmol) of hydroxytyrosol and 61.3 mg (0.32 mmol) EDC were dissolved in 30 mL of tetrahydrofuran under nitrogen atmosphere. 56.3 mg (0.38 mmol) of cinnamic acid was dissolved in 20 mL of tetrahydrofuran, and slowly added dropwise to the reaction mixture by a separatory funnel. After the completion of the dropwise addition, the temperature was raised to 80° C., and the reaction was carried out for 4 hours. Thin layer chromatography was used to track the reaction to completion, heating was stopped, and the protective device was removed. The concentrated reaction mixture was washed wash water, extracted with ethyl acetate, dried and concentrated to obtain a crude product. The crude product was purified by silica gel column chromatography with petroleum ether:ethyl acetate=3:10 as eluent, and the eluent was concentrated under reduced pressure and dried to obtain 53.6 mg of the title compound, a total yield of 58.95%.

EXAMPLE 4

Preparation of Compound
(Z)-3,4-Dihydroxyphenethyl 3-Phenylacrylate

In a 100 mL three-necked flask, 49.3 mg (0.32 mmol) of hydroxytyrosol and 61.3 mg (0.32 mmol) EDC were dissolved in 30 mL of toluene under nitrogen atmosphere. 51.8 mg (0.35 mmol) of cinnamic acid was dissolved in 20 mL of toluene, and slowly added dropwise to the reaction mixture by a separatory funnel. After the completion of the dropwise addition, the temperature was raised to 75° C., and the reaction was carried out for 6 hours. Thin layer chromatography was used to track the reaction to completion, heating was stopped, and the protective device was removed. The concentrated reaction mixture was washed wash water, extracted with ethyl acetate, dried and concentrated to obtain a crude product. The crude product was purified by silica gel column chromatography with petroleum ether:ethyl acetate=3:10 as eluent, and the eluent was concentrated under reduced pressure and dried to obtain 50.7 mg of the title compound, a total yield of 55.77%.

EXAMPLE 5

Preparation of Compound
(Z)-3,4-Dihydroxyphenethyl 3-Phenylacrylate

In a 100 mL three-necked flask, 49.3 mg (0.32 mmol) of hydroxytyrosol and 61.3 mg (0.32 mmol) EDC were dissolved in 30 mL of acetonitrile under nitrogen atmosphere. 51.8 mg (0.35 mmol) of cinnamic acid was dissolved in 20 mL of acetonitrile, and slowly added dropwise to the reaction mixture by a separatory funnel. After the completion of the dropwise addition, the temperature was raised to 60° C., and the reaction was carried out for 7 hours. Thin layer chromatography was used to track the reaction to completion, heating was stopped, and the protective device was removed. The concentrated reaction mixture was washed wash water, extracted with ethyl acetate, dried and concentrated to obtain a crude product. The crude product was purified by silica gel column chromatography with petroleum ether:ethyl acetate=3:10 as eluent, and the eluent was concentrated under reduced pressure and dried to obtain 51.0 mg of the title compound, a total yield of 56.14%.

EXAMPLE 6

Preparation of Compound
(Z)-3,4-Dihydroxyphenethyl 3-Phenylacrylate

In a 100 mL three-necked flask, 49.3 mg (0.32 mmol) of hydroxytyrosol and 61.3 mg (0.32 mmol) EDC were dissolved in 30 mL of tetrahydrofuran under nitrogen atmosphere. 51.8 mg (0.35 mmol) of cinnamic acid was dissolved in 20 mL of tetrahydrofuran, and slowly added dropwise to the reaction mixture by a separatory funnel. After the completion of the dropwise addition, the temperature was raised to 70° C., and the reaction was carried out for 8 hours. Thin layer chromatography was used to track the reaction to completion, heating was stopped, and the protective device was removed. The concentrated reaction mixture was washed wash water, extracted with ethyl acetate, dried and concentrated to obtain a crude product. The crude product was purified by silica gel column chromatography with petroleum ether:ethyl acetate=3:10 as eluent, and the eluent was concentrated under reduced pressure and dried to obtain 50.3 mg of the title compound, a total yield of 55.38%.

EXAMPLE 7

Preparation of Compound
(Z)-3,4-Dihydroxyphenethyl 3-Phenylacrylate

In a 100 mL three-necked flask, 49.3 mg (0.32 mmol) of hydroxytyrosol, 51.8 mg (0.35 mmol) of cinnamic acid and 5.5 mg (0.003 mmol) silicomolybdic acid were dissolved in 50 mL of 1-butyl-3-methylimidazolium tetrafluoroborate under nitrogen atmosphere. After full dissolution, the reaction was carried out at 25° C. for 8 hours. Thin layer chromatography was used to track the reaction to completion, heating was stopped, and the protective device was removed. The reaction mixture was allowed to separate into layers to give a crude product. The crude product was recrystallized with 50 mL methanol, and filtered and dried to obtain 78.3 mg of the titled compound, a total yield of 86.11%.

EXAMPLE 8

Preparation of Compound
(Z)-3,4-Dihydroxyphenethyl 3-Phenylacrylate

In a 100 mL three-necked flask, 49.3 mg (0.32 mmol) of hydroxytyrosol, 51.8 mg (0.35 mmol) of cinnamic acid and 5.5 mg (0.003 mmol) silicomolybdic acid were dissolved in 50 mL of 1-butyl-3-methylimidazolium tetrafluoroborate under nitrogen atmosphere. After full dissolution, the reaction was carried out at 50° C. for 4 hours. Thin layer chromatography was used to track the reaction to completion, heating was stopped, and the protective device was removed. The reaction mixture was allowed to separate into layers to give a crude product. The crude product was recrystallized with 50 mL methanol, and filtered and dried to obtain 75.0 mg of the titled compound, a total yield of 82.54%.

EXAMPLE 9

Preparation of Compound
(Z)-3,4-Dihydroxyphenethyl 3-Phenylacrylate

In a 100 mL three-necked flask, 49.3 mg (0.32 mmol) of hydroxytyrosol, 51.8 mg (0.35 mmol) of cinnamic acid and 5.5 mg (0.003 mmol) silicomolybdic acid were dissolved in 50 mL of 1-hexyl-3-methylimidazolium tetrafluoroborate under nitrogen atmosphere. After full dissolution, the reaction was carried out at 25° C. for 8 hours. Thin layer chromatography was used to track the reaction to completion, heating was stopped, and the protective device was removed. The reaction mixture was allowed to separate into layers to give a crude product. The crude product was recrystallized with 50 mL methanol, and filtered and dried to obtain 72.6 mg of the titled compound, a total yield of 79.87%.

EXAMPLE 10

Preparation of Compound
(Z)-3,4-Dihydroxyphenethyl 3-Phenylacrylate

In a 100 mL three-necked flask, 49.3 mg (0.32 mmol) of hydroxytyrosol, 51.8 mg (0.35 mmol) of cinnamic acid and 5.5 mg (0.003 mmol) silicomolybdic acid were dissolved in 50 mL of 1-hexyl-3-methylimidazolium tetrafluoroborate under nitrogen atmosphere. After full dissolution, the reaction was carried out at 50° C. for 4 hours. Thin layer chromatography was used to track the reaction to completion, heating was stopped, and the protective device was removed. The reaction mixture was allowed to separate into layers to give a crude product. The crude product was recrystallized with 50 mL methanol, and filtered and dried to obtain 71.7 mg of the titled compound, a total yield of 78.59%.

EXAMPLE 11

Preparation of Compound
(Z)-3,4-Dihydroxyphenethyl 3-Phenylacrylate

In a 100 mL three-necked flask, 49.3 mg (0.32 mmol) of hydroxytyrosol, 51.8 mg (0.35 mmol) of cinnamic acid and 5.5 mg (0.003 mmol) silicomolybdic acid were dissolved in 50 mL of 1-octyl-3-methylimidazolium hexafluorophosphate under nitrogen atmosphere. After full dissolution, the reaction was carried out at 25° C. for 8 hours. Thin layer chromatography was used to track the reaction to completion, heating was stopped, and the protective device was removed. The reaction mixture was allowed to separate into layers to give a crude product. The crude product was recrystallized with 50 mL methanol, and filtered and dried to obtain 74.9 mg of the titled compound, a total yield of 82.41%.

EXAMPLE 12

Preparation of Compound
(Z)-3,4-Dihydroxyphenethyl 3-Phenylacrylate

In a 100 mL three-necked flask, 49.3 mg (0.32 mmol) of hydroxytyrosol, 51.8 mg (0.35 mmol) of cinnamic acid and 5.5 mg (0.003 mmol) silicomolybdic acid were dissolved in 50 mL of 1-octyl-3-methylimidazolium hexafluorophosphate under nitrogen atmosphere. After full dissolution, the reaction was carried out at 50° C. for 4 hours. Thin layer chromatography was used to track the reaction to completion, heating was stopped, and the protective device was removed. The reaction mixture was allowed to separate into layers to give a crude product. The crude product was recrystallized with 50 mL methanol, and filtered and dried to obtain 73.4 mg of the titled compound, a total yield of 80.76%.

EXAMPLE 13

The antioxidant activity of the hydroxytyrosol cinnamic acid ester was measured by a DPPH radical scavenging activity assay.

2,2-Diphenyl-1-picryl hydrazyl (DPPH) is an organic compound composed of a stable organic radical. In the DPPH molecule, due to the presence of multiple electron-withdrawing —$NO_2$ and large π bonds of the benzene ring, nitrogen free radical is stabilized. Its methanol solution is purple and has a maximum absorption peak at 517 nm. After the addition of an antioxidant, DPPH captures an electron to be paired with the free electron, and the purple fades and turns into a yellow substance. The absorption at 517 nm disappears, and the degree of fading is quantitatively related to the number of electrons it captures. Based on this principle, a spectrophotometer is used to detect the change of the absorbance of the DPPH radical and the sample solution, and the ability of the sample to provide hydrogen atoms and scavenge free radicals can be measured.

Preparation of DPPH Solution:

measuring exact amount of 2,2-diphenyl-1-picryl hydrazyl (DPPH) and dissolving in toluene to prepare a 0.2 mmoL/L DPPH solution, stored at 0° C. in dark.

Preparation of Test Solution:

Vc (positive control), hydroxytyrosol cinnamic acid ester (sample), hydroxytyrosol (control) and cinnamic acid (control). The sample solution was subjected to gradient dilution with toluene, and three sets of controls were separately dissolved in a test tube with a certain amount of toluene to prepare the same concentration gradient as the sample. The corresponding three groups of control solutions were obtained (gradient settings are shown in Table 1).

TABLE 1

Dilution gradient of the test solution

| Number | Test solution | Concentration gradient/ppm |
|---|---|---|
| Vc | Vc | 1.76, 8.80, 21.12, 42.24, 79.20, 112.64, 281.60, 492.80, 792.00, 915.20 |
| A | Hydroxytyrosol cinnamic acid ester | 1.76, 8.80, 21.12, 42.24, 79.20, 112.64, 281.60, 492.80, 792.00, 915.20 |
| B | Hydroxytyrosol | 1.76, 8.80, 21.12, 42.24, 79.20, 112.64, 281.60, 492.80, 792.00, 915.20 |
| C | Cinnamic acid | 1.76, 8.80, 21.12, 42.24, 79.20, 112.64, 281.60, 492.80, 792.00, 915.20 |

Specific Steps:

Sample liquid absorbance measurement: Take 2 mL of sample solution (Table 1 Vc, B, C), add 2 mL of DPPH solution with concentration of $2 \times 10^{-4}$ moL/L, mix and react in the dark at room temperature for 30 min, adjust to zero with toluene, and measure at 517 nm. The absorbance $Ai$ was simultaneously measured for the absorbance $Aj$ of 2 mL of toluene mixed with 2 mL of the sample solution and the absorbance $Ao$ of 2 mL of DPPH solution mixed with 2 mL of toluene (The experimental results are shown in Table 2).

TABLE 2

Absorbance test results of each test solution

| Sample | Absorbance | Concentration/ppm | | | | | | | | | |
|---|---|---|---|---|---|---|---|---|---|---|---|
| | | 1.76 | 8.80 | 21.12 | 42.24 | 79.20 | 112.64 | 281.60 | 492.80 | 792.00 | 915.20 |
| Vc | Ai | 0.718 | 0.624 | 0.222 | 0.142 | 0.091 | 0.078 | 0.076 | 0.070 | 0.074 | 0.065 |
| | Aj | 0.068 | 0.061 | 0.050 | 0.054 | 0.069 | 0.057 | 0.062 | 0.062 | 0.066 | 0.059 |
| | Ao | 0.846 | | | | | | | | | |
| A | Ai | 0.794 | 0.755 | 0.639 | 0.525 | 0.440 | 0.320 | 0.264 | 0.205 | 0.186 | 0.172 |
| | Aj | 0.049 | 0.043 | 0.057 | 0.043 | 0.057 | 0.052 | 0.061 | 0.043 | 0.052 | 0.044 |
| | Ao | 0.853 | | | | | | | | | |
| B | Ai | 0.918 | 0.904 | 0.810 | 0.739 | 0.630 | 0.580 | 0.403 | 0.365 | 0.268 | 0.254 |
| | Aj | 0.053 | 0.046 | 0.047 | 0.039 | 0.060 | 0.055 | 0.041 | 0.046 | 0.035 | 0.037 |
| | Ao | 0.935 | | | | | | | | | |
| C | Ai | 0.897 | 0.868 | 0.820 | 0.771 | 0.672 | 0.604 | 0.457 | 0.404 | 0.304 | 0.294 |
| | Aj | 0.052 | 0.039 | 0.047 | 0.051 | 0.055 | 0.049 | 0.042 | 0.039 | 0.038 | 0.040 |
| | Ao | 0.904 | | | | | | | | | |

Clearance calculation: Clearance Rate (%)=[1−($Ai$−$Aj$)/$Ao$]*100%

TABLE 3

DPPH clearance rate experiment results

| Concentration/ ppm | Clearance rate/% (n = 3) | | | |
|---|---|---|---|---|
| | Vc | A | B | C |
| 1.76 | 23.16 | 0.56 | 7.42 | 6.45 |
| 8.80 | 33.47 | 16.52 | 8.16 | 8.20 |
| 21.12 | 79.63 | 31.75 | 18.43 | 14.52 |
| 42.24 | 89.55 | 43.52 | 25.10 | 20.33 |
| 79.20 | 97.42 | 55.11 | 38.99 | 31.75 |
| 112.64 | 97.53 | 68.53 | 43.87 | 38.62 |
| 281.60 | 98.29 | 76.22 | 61.25 | 54.12 |
| 492.80 | 99.06 | 80.95 | 65.88 | 59.60 |

TABLE 3-continued

DPPH clearance rate experiment results

| Concentration/ | Clearance rate/% (n = 3) | | | |
|---|---|---|---|---|
| ppm | Vc | A | B | C |
| 792.00 | 99.10 | 84.32 | 75.03 | 70.53 |
| 915.20 | 99.28 | 85.03 | 76.76 | 71.89 |

EXAMPLE 14

Antibacterial Activity Test

The minimal inhibitory concentrations (MIC) of the compounds were determined by microbroth dilution method with gentamicin, cefazolin sodium and ceftriaxone sodium as positive control.

The experimental strains included methicillin-resistant Gram-positive bacteria: methicillin-resistant *Straphylococcus aureus* MRSA 18-222, 18-575; multiple drug-resistant Gram-negative bacteria: vancomycin-resistant *Enterococci* VRE 18-80, 18-94, multidrug-resistant *Pseudomonas aeruginosa* MDR-PA 18-1774, 18-202, carbapenem-resistant *Acinetobacter baumannii* CR-AB 18-183, 18-560. All the experimental strains were donated by Huashan Hospital affiliated to Fudan University (Institute of antibiotics, Fudan University) and used after routine identification.

Preparation of Test Strains:

Preparation of MHB medium: 20.0 g MHB medium was added to 1 L distilled water, boiled until completely dissolved, packed in conical bottles and sterilized at 121° C. for 15 min.

The experimental strain was cultured to the logarithmic growth phase: under aseptic condition, the experimental strain was inoculated into 100 mL MHB medium and incubated in a constant temperature and humidity incubator at 37° C. for 20-22 hours.

Preparation of storage solution: weighing the sample to be tested, dissolving it with 1% DMSO solution, preparing a storage solution with a concentration of 2560 μg/mL, weighing a positive reference substance, dissolving it with aseptic distilled water, and configuring a storage solution with a concentration of 2560 μg/mL.

Preparation of bacterial suspension: under aseptic condition, the experimental strains cultured to logarithmic growth phase were adjusted to 0.5 MCF turbidity standard with MHB medium and diluted according to 1:10, and the bacterial suspension with concentration of $10^6$ CFU/mL was prepared for standby.

Dilution of storage solution and inoculation of experimental strain: under aseptic condition, the storage solution was diluted to 256 μg/mL solution. Taking a sterile 96-well plate, adding 200 μL MHB medium to the 12th well, and adding 100 μL MHB medium to each well. Adding 100 μL of positive control solution to the first well, mixing well, and taking 100 μL and discard. Adding 100 μL of the compound sample solution to the second well, mixing well, and then pipetting 100 μL to the third well. After mixing, pipetting 100 μL to the fourth well, and diluting to the 11th well in the same way. Finally, 100 μL was pipetted from the 11th well and discarded. The 12th hole was the growth control without drugs. The concentration of the positive reference substance was 128 μg/mL, the concentrations of the sample solution were 128, 64, 16, 8, 4, 2, 1, 0.5, 0.25 μg/mL respectively. Then, 100 μL of the prepared bacterial suspension was added to each well, so that the final concentration of the bacterial liquid in each well was $5\times10^5$ CFU/mL.

Incubation: Covering the 96-well plate inoculated with the experimental strains, and incubating in a constant temperature and humidity box at 37° C. for 20-22 hours.

Interpretation of the MIC endpoint: The concentration that can completely inhibit the growth of bacteria in a 96-well plate under a black background is the lowest inhibitory concentration of the sample against the bacteria.

Figure 2:
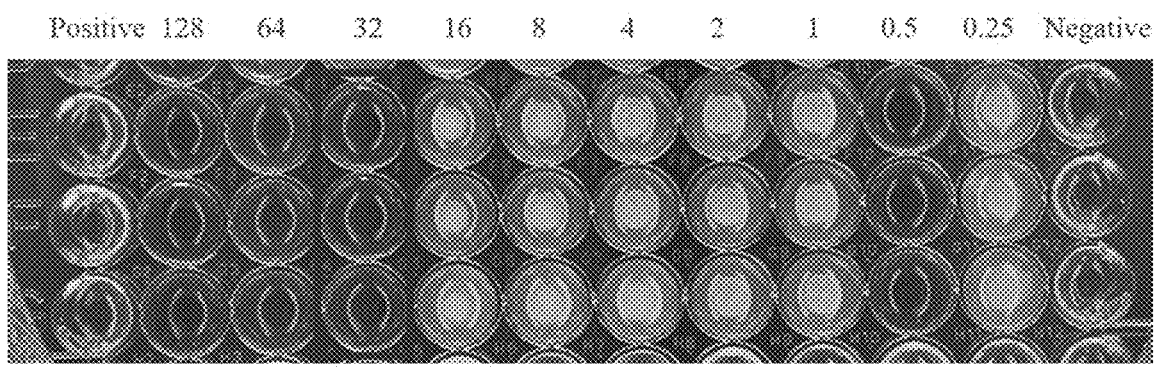
FIG. 2 shows the in vitro antibacterial activity of hydroxytyrosol cinnamic acid ester against drug-resistant bacteria MRSA 18-222.
Figure 3:
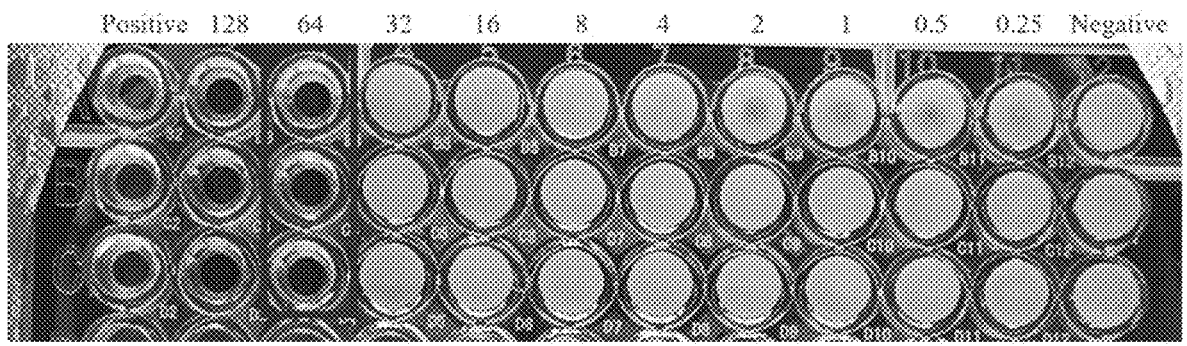
FIG. 3 shows the in vitro antibacterial activity of hydroxytyrosol cinnamic acid ester against drug-resistant bacteria MDR-PA 18-174.

In FIGS. 2-3, the twelve wells represent twelve groups, from left to right, positive, 128 μg/mL, 64 μg/mL, 32 μg/mL, 16 μg/mL, 8 μg/mL, 4 μg/mL, 2 μg/mL, 1 μg/mL, 0.25 μg/mL, 0.0625 μg/mL, Negative. FIG. 2 shows the in vitro antibacterial activity of hydroxytyrosol cinnamic acid ester against drug-resistant bacteria MRSA 18-222. FIG. 3 shows the in vitro antibacterial activity of hydroxytyrosol cinnamic acid ester against drug-resistant bacteria MDR-PA 18-174. The results are shown in Table 4.

TABLE 4

Minimum bacteriostatic concentration of test drug and positive drug (μg · mL$^{-1}$)

| | Strain | | | | | | | |
|---|---|---|---|---|---|---|---|---|
| | MRSA | | VRE | | MDR-PA | | CR-AB | |
| Sample | 18-222 | 18-575 | 18-80 | 18-94 | 18-174 | 18-202 | 18-183 | 18-560 |
| Hydroxytyrosol cinnamic acid ester | 32 | >128 | >128 | >128 | 64 | >128 | >128 | >128 |
| Gentamicin | 128 | 2 | 0.0625 | >128 | 0.0625 | 0.0625 | >128 | >128 |
| Cefazolin sodium | >128 | >128 | 32 | >128 | 8 | 128 | >128 | >128 |
| Ceftriaxone sodium | >128 | >128 | 8 | >128 | 128 | 16 | >128 | >128 |
| Hydroxytyrosol | >128 | >128 | >128 | >128 | >128 | >128 | >128 | >128 |
| Cinnamic acid | >128 | >128 | >128 | >128 | >128 | >128 | >128 | >128 |

As shown in FIGS. 2-3 and Table 4, hydroxytyrosol and cinnamic acid had no inhibitory effect on drug-resistant bacteria, while hydroxytyrosol cinnamic acid ester showed a strong inhibitory effect on multi-drug resistant *Pseudomonas aeruginosa* MDR-PA (MIC=64 μg/mL) and multi-drug resistant *Straphylococcus aureus* MRSA (MIC=32 μg/mL). In summary, the hydroxytyrosol cinnamic acid ester of the present invention can be used as antibacterial drug candidates for multidrug resistant *Pseudomonas aeruginosa* and multidrug resistant *Straphylococcus aureus*, as well as further preclinical research. At the same time, the derivative has excellent antioxidant activity, further expanding its production and sales market.

What is claimed is:

1. A method of preparing a compound of formula (I), comprising:

reacting a compound of formula (II) with a compound of formula (III) to obtain the compound of formula (I):

wherein the reaction of the compound of formula (II) with the compound of formula (III) comprises the following steps:

placing the compound of formula (II) and the compound of formula (III), in a molar ratio of 1:1 to 1:1.3, in a reactor;

adding an organic solvent and a catalytic amount of EDC under nitrogen atmosphere to obtain a reaction mixture; and heating the reaction mixture at 50-80° C. for 4-8 hours; and purifying the crude product on a silica gel fresh chromatography column with petroleum ether and ethyl acetate as an eluent to obtain the compound of formula (I); or wherein the reaction of the compound of formula (II) with the compound of formula (III) comprises the following steps:

placing the compound of formula (II), a catalyst, and an ionic liquid in a reactor under nitrogen atmosphere, the catalyst being 12-molybdosilicic acid hydrate ($H_6Mo_{12}O_{41}Si$);

adding the compound of formula (III) to the reactor to form a reaction mixture;

heating the reaction mixture at 25-50° C. for 5-10 hours;

placing the reaction mixture in a separating funnel to separate a crude product;

purifying the crude product by recrystallization in methanol to obtain the compound of formula (I); and recycling the ionic liquid.

2. The method of claim 1, wherein the organic solvent is toluene, tetrahydrofuran or acetonitrile.

3. The method of claim 2, wherein the organic solvent is acetonitrile.

4. The method of claim 1, wherein the molar ratio of the compound of formula (II) and the compound of formula (III) is 1:1.1.

5. The method of claim 1, wherein the reaction mixture is heated at 70° C.

6. The method of claim 1, wherein the reaction mixture is heated for 6 hours.

7. The method of claim 1, wherein the eluent is petroleum ether:ethyl acetate=3:10.

8. The method of claim 1, wherein the ionic liquid is 1-octyl-3-methylimida-zolium hexafluorophosphate, 1-hexyl-3-methylimidazolium tetrafluoroborate, or 1-butyl-3-methylimidazolium tetrafluoroborate ([BMIM][$BF_4$]).

9. The method of claim 8, wherein the ionic liquid is the ionic liquid is 1-butyl-3-methylimidazolium tetrafluoroborate ([BMIM][$BF_4$]).

10. The method of claim 1, wherein the compound of formula (II) and the compound (III) have a molar ratio of 1:1 to 1:1.3.

11. The method of claim 10, wherein the molar ratio of the compound of formula (II) and the compound of formula (III) is 1:1.1.

12. The method of claim 1, wherein the reaction mixture is heated at 25° C.

13. The method of claim 1, wherein the reaction mixture is heated for 8 hours.

* * * * *